United States Patent [19]

Rockey

[11] Patent Number: 4,641,653
[45] Date of Patent: Feb. 10, 1987

[54] MEDICAL SLEEVE

[76] Inventor: Arthur G. Rockey, 3438 Sharon Rd., Charlotte, N.C. 28211

[21] Appl. No.: 702,828

[22] Filed: Feb. 19, 1985

Related U.S. Application Data

[63] Continuation-in-part of Ser. No. 216,989, Dec. 16, 1980, Pat. No. 4,501,264, which is a continuation of Ser. No. 912,010, Jun. 2, 1978, abandoned.

[51] Int. Cl.$^4$ .................................. A61M 29/02
[52] U.S. Cl. ............................... 128/344; 604/96
[58] Field of Search ............... 128/1 R, 92 C, 303 R, 128/30.11, 325, 334 R, 344; 604/96–103, 8, 175

[56] References Cited

U.S. PATENT DOCUMENTS

| | | | |
|---|---|---|---|
| 3,045,677 | 7/1962 | Wallace | 128/344 |
| 3,046,988 | 7/1962 | Moreau et al. | 128/344 |
| 3,834,394 | 9/1974 | Hunter et al. | 128/325 |
| 3,991,767 | 11/1976 | Miller, Jr. et al. | 128/334 R |
| 4,085,757 | 4/1978 | Pevsner | 604/96 |
| 4,133,315 | 1/1979 | Berman et al. | 128/303 R |
| 4,134,405 | 1/1979 | Smit | 128/303 R |
| 4,140,126 | 2/1979 | Choudhury | 604/175 |
| 4,141,364 | 2/1979 | Schultze | 128/344 |
| 4,364,392 | 12/1982 | strother et al. | 128/325 |
| 4,515,587 | 5/1985 | Schiff | 604/282 |

OTHER PUBLICATIONS

New Products and Processes in *Polymer News*, vol. 7, No. 5, May 1981, p. 219.

Primary Examiner—C. Fred Rosenbaum
Assistant Examiner—Jerome R. Smith, Jr.
Attorney, Agent, or Firm—Pearne, Gordon, McCoy & Granger

[57] ABSTRACT

A method and article for medical diagnosis and/or treatment of body disorders, comprising a sleeve unit insertable in a natural body vessel to isolate material flowing into the vessel from direct contact with the interior surface of the vessel. When applied to the treatment of obesity, the sleeve is disposed along a zone in the digestive tract to interfere with the digestive or absorptive function of that zone and thereby reduce net caloric intake.

2 Claims, 10 Drawing Figures

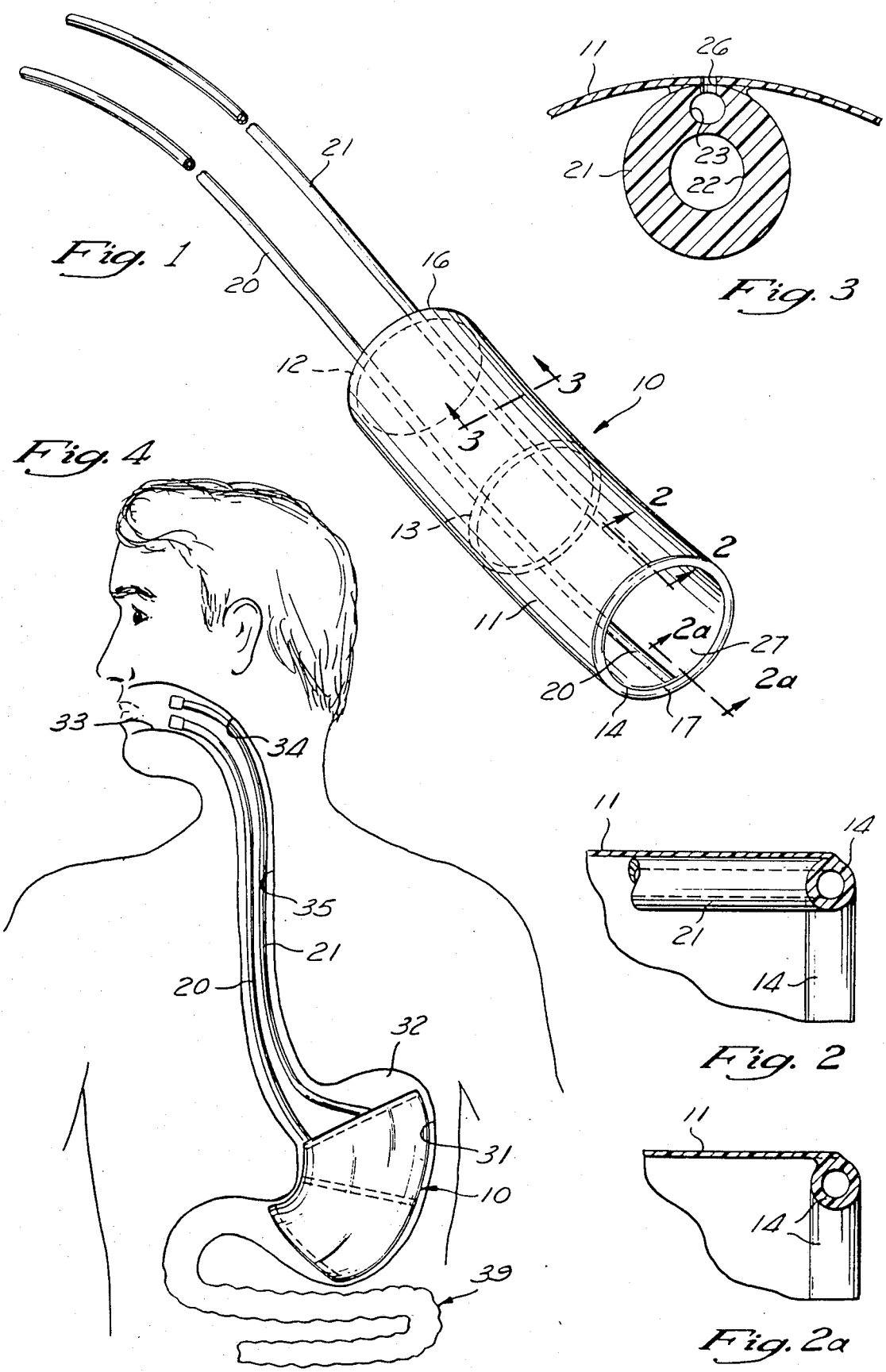

MEDICAL SLEEVE

This is a continuation-in-part of my copending application Ser. No. 216,989, filed Dec. 16, 1980, now U.S. Pat. No. 4,501,264 which is a continuation of prior application Ser. No. 912,010, filed June 2, 1978, now abandoned.

BACKGROUND OF THE INVENTION

In the diagnosis and/or treatment of disorders of the body, it is known to physically alter the condition or function of hollow viscera or other internal body vessels. Surgical procedures on such vessels include reconstruction of natural tissue, substitution and bypass techniques with natural or artificial implants. Surgery is recognized as always carrying some degree of risk to the patient, both during its actual performance and in postoperative complications or side effects. These risks, of course, are of major concern when the surgery involves the invasion of the great cavity of the trunk of the human body. This is especially ture in treatment of such viscera as the heart, liver, or intestines, and in particular when such surgery involves these organs themselves.

In surgical treatment of obesity, for example, the abdominal cavity is exposed to allow reconstruction of the digestive tract, in essence, to reduce the internal surface area available for food digestion or absorption of digested substances. The former technique, a gastric bypass, may be accomplished by anastomosing a minor portion of the stomach to the jejunum while leaving the major portion connected to the duodenum. The latter of these techniques, an intestinal bypass, involves the short-circuiting of a majority of the combined lengths of the jejunum and ileum by connecting the first part of the jejunum to the last part of the ileum.

Both of these operations are deemed to involve such high risk to the patient that they are considered only as a lifesaving undertaking for morbidly obese individuals. Beyond statistically significant operative and overall mortality rates, reported complications following the gastric bypass include marginal ulcers and wound infections. The intestinal bypass involves similar mortality rates and, reportedly, a greater number of postoperative complications and side effects. These include pulmonary emboli, wound infections, gastrointestinal hemorrhage, renal failure, and numerous other disorders. The nature, severity, and frequency of these problems have in fact led to doubts as to the advisability of the techniques for treatment of obesity.

SUMMARY OF THE INVENTION

The invention provides a method and means for isolating the internal walls of hollow viscera or other body vessels from contact with materials, both fluids and solids, occurring naturally, ingested, or otherwise introduced into a body vessel. Isolation of a body vessel, according to the invention, is achieved by positioning and anchoring a sleeve, impervious to materials sought to be isolated within the vessel, in such a manner that the sleeve, at least adjacent its upstream end, is in sealing engagement with the surrounding interior tissue of the vessel. Material otherwise normally flowing into the vessel and being capable of interracting with the vessel to the detriment of the patient's health is thereby contained and rendered ineffectual or on unaffected by the vessel.

An important application of the invention is the nonsurgical treatment of obesity through reduction in the effective natural surface area of the digestive tract. In one disclosed embodiment, a sleeve impervious to both gastric secretions and food substances is disposed within the stomach in a manner which prevents contact between these gastric secretions and food substances. More specifically, the sleeve acts as a liner for at least a portion of the internal stomach area while also providing a conduit for food passing through the stomach. The sleeve, which is capable of establishing a circumferential, substantially fluidtight seal with the walls of the stomach adjacent its upstream end, may be any desired length so that a suitable portion of the internal stomach area is rendered ineffectual in the digestive process. Consequently, the sleeve is operative to limit the efficiency of food absorption in the small intestine.

As disclosed, the sleeve may be introduced into the stomach through the oral cavity and esophagus. In the preferred embodiment, the sleeve is sufficiently flexible to be collapsed into a unit of relatively low bulk for ease of passage through the posterior pharynx and esophagus. Upon reaching a desired position in the stomach, the sleeve is expanded by means carried with the sleeve, including a flexible tube trailing the sleeve. A source of pressurized fluid external of the patient's body is operably connected to the expanding means through this trailing tube to expand the sleeve into sealing engagement with the walls of the stomach. The sleeve may be additionally restrained against further movement along the digestive tract by anchoring the trailing tube or a separate parallel element upstream in the digestive tract.

The tissue isolating function of the disclosed sleeve, in addition to control of the mechanism of digestion, has numerous other applications in diagnosis or treatment of body disorders. For example, the sleeve may be used to chemically and/or physically protect tissue which has been ulcerated, herniated, fissured, or the like from natural body fluids. Ruptured blood vessels or aneurysms may be protected from further damage and allowed to heal by isolating the effect of normal blood pressure from the vessel by containing it within the sleeve.

Stenosis or a sclerotic closing of an artery may be expanded from within by the use of internal compression while still allowing blood to pass through, especially in those individuals whose disease is so far advanced that a graft could not be sutured to the distal portion of the vessel. Still further, where desired, one or more tubes connected to the sleeve may be arranged to provide communication between the annular zone intermediate the protected vessel and the outer surface of the sleeve for introduction of medicines or aspiration of fluids from the zone.

BRIEF DESCRIPTION OF THE DRAWINGS

FIG. 1 is a perspective view of a vessel-insertable medical sleeve unit constructed in accordance with the invention;

FIG. 2 is a fragmentary, cross sectional view on an enlarged scale through the wall of the sleeve unit, taken along the line 2—2 of FIG. 1;

FIG. 2a is a fragmentary, cross sectional view similar to FIG. 3, taken along the line $2_a$—$2_a$ of FIG. 1;

FIG. 3 is a fragmentary, cross sectional view on an enlarged scale, taken along the line 3—3 of FIG. 1 of a trailing filament of the sleeve unit;

FIG. 4 is a schematic illustration of a manner of use of the sleeve to control obesity;

DESCRIPTION OF THE PREFERRED EMBODIMENT

Figure 5:
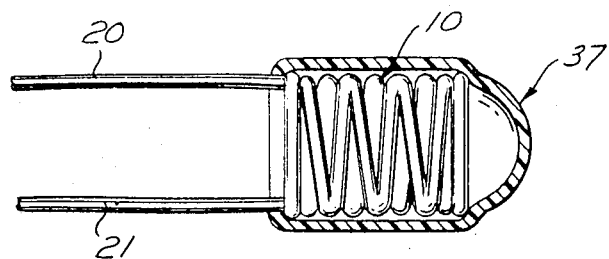
FIG. 5 is a view of the sleeve unit in a compacted condition and contained within a dilator shell for installation.

Referring now to the drawings, and in particular to FIG. 1, there is shown a sleeve unit 10 in the form of a cylindrical, tubular sheath 11 and one or more inflator ring balloons 12-14. The sheath 11 in the illustrated example if a flexible membrane of nontoxic material impervious and chemically resistant to body fluids which it is expected to encounter. The sheath material is selected from a variety of known plastic and/or elastomeric substances. The sheath 11 may be extruded, rolled, or otherwise formed, as desired, into a tube with or without a longitudinal seam or seams.

The inflator ring balloons 12-14 as indicated in FIG. 1 are flexible, hollow, torroid-like elements spaced axially along the interior of the sheath 11. As indicated, the rings 12 and 14 are adjacent opposite ends 16 and 17 of the sheath 11. The ring balloons 12-14 may be formed of a material the same as or like that of the sheath 11, and are either integrally formed thereon or are bonded thereto by heat, adhesive, solvent or like means. While the sheath 11 is illustrated as a cylinder, it will be understood that it may take other configurations, such as a frustum or a sphere truncated adjacent opposite poles, or a tubular elbow of constant or varying diameter. The sleeve unit 10 includes at least one, and preferably two, trailing hollow filaments 20,21 connected thereto by bonding or other suitable means. These filaments 20,21 may be made of the same or similar material as the sheath 11. In the illustrated case, each of the filaments 20-21 includes a central lumen 22 and an auxiliary lumen 23. When desired or necessary, additional lumens may be disposed in the wall of each filament 20-21. Ideally, one of the filaments 20 has its central lumen 22 in fluid communication with an upstream one 12 of the ring balloons, while the other filament 21 has its central lumen 22 in fluid communication with the remaining ring balloons 13 and 14.

As suggested in FIG. 3, longitudinally spaced, generally radial passages 26 provide communication from the auxiliary lumens 23 of each filament 20, 21 through the adjacent wall of the sheath 11 to points external of the sleeve unit 10. The exterior surface of the filaments 20,21 and internal surface of the sheath 11 are sealed to one another by suitable means, such as bonding or the like, at their points of tangency so that fluids in the auxiliary lumens cannot escape into the interior, designated 27, of the sheath 11 at the radial passages or apertures 26.

Figure 6:
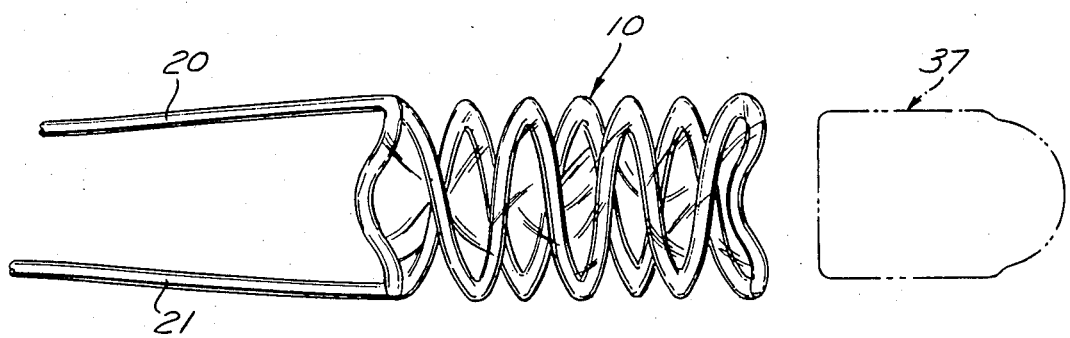
FIG. 6 is a view of the sleeve unit depicting an intermediate configuration in a progressive sequence of expansion from the condition of FIG. 4.

The sleeve unit 10 is implanted in a body vessel in order to isolate the walls of such vessel from fluids normally flowing into it. FIG. 4 illustrates a manner of use of the sleeve unit 10 to isolate the internal surface area or lumen, designated 31, of a human stomach 32 and its secretions from food substances passing through it. The sleeve unit 10 is implanted in the stomach 32 in a nonsurgical manner by passing it through an oral cavity 33, pharynx 34, and esophagus 35. To facilitate introduction of the sleeve unit 10 into the stomach 32, the sleeve unit is folded on itself accordion fashion to reduce its length and diameter. In its folded or compacted state, the sleeve unit 10 is contained within a dilator shell or cup 37 (FIGS. 5 and 6). The dilator shell 37 has a rounded profile for ease of passage through the natural lumen of the digestive tract, generally indicated at 39 (FIG. 4). The dilator shell 37 carrying the collapsed sleeve unit 10 is inserted through the epiglotis, whereupon natural swallowing action allows it to be readily advanced into the stomach 32.

Figure 7:
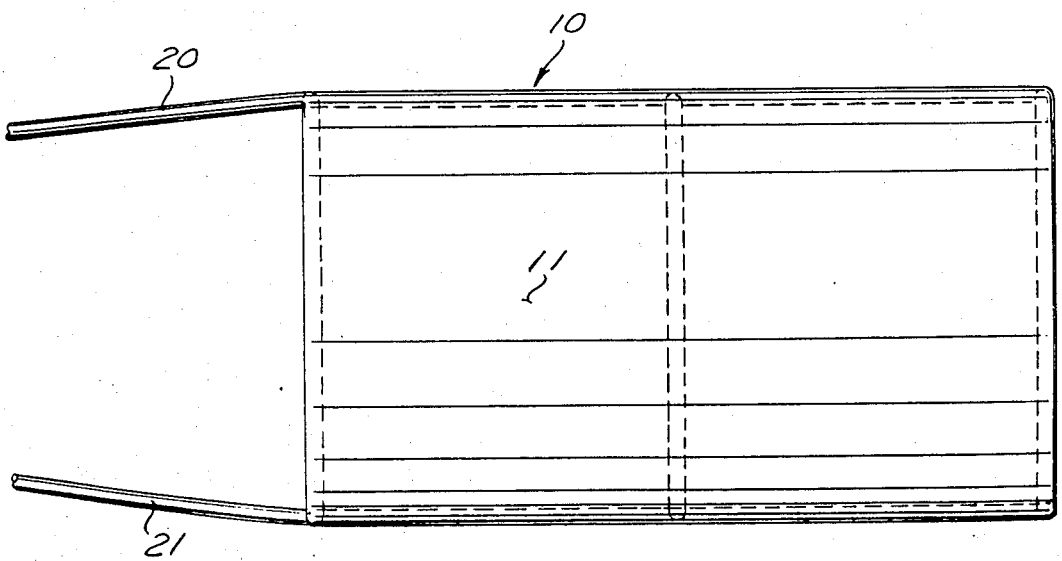
FIG. 7 is a view of the sleeve progressed in its transition from FIG. 5 through FIG. 6 to a fully expanded configuration essentially corresponding to FIG. 4.

Upon reaching the stomach 32, one or both of the central lumens 22 of the filaments 20,21 are connected to a source of pressurized fluid, such as air, ordinarily external of the oral cavity 33. Lower sections of the filaments 20, 21 longitudinally associated with the sheath 11 develop forces upon pressurization, tending to unfold themselves along with the sheath. FIG. 6 depicts this action, wherein the dilator shell 37 is released from the sleeve unit 10 and allowed to pass through the lower portion of the digestive tract 39. The sleeve unit 10 in a continuous sequence of movement expands from the intermediate position of FIG. 6 to that of FIG. 7.

The final position of the sleeve unit 10 in the stomach 32 may be adjusted by pumping fluid through the auxiliary lumens 23 in such a manner that it issues from the passages 26 as a jet developing a reaction force to shift the adjacent area of the sleeve unit in one direction or another, depending on the orientation of the passages. These passages 26 may be provided with either an axial or tangential component in their orientation with respect to the axial direction of the sleeve to cause corresponding axial or turning movement of the sleeve. Preferably, the sleeve unit 10, including the filaments 20, 21 and ring balloons 12-14, is provided with sufficient radiopaque material to permit external observation of its position and configuration. When the position of the sleeve unit 10 is satisfactory, the ring balloons 12-14 are finally inflated through the central filament lumens 22, again by a source of pressurized fluid external of the patient's body. Inflation of the ring balloons 12-14 causes them, in the manner of circumferential stiffening ribs, to fully expand the sleeve into tight sealing engagement with the interior surface 31 of the stomach vessel 32. The ends of the filaments 20,21 distal from the sleeve unit 10 are anchored to a posterior tooth or prosthesis by suitable fastening means or are sutured in place. The central or main lumens 22 of the filaments 20,21 are closed at these anchoring points by heat sealing, plugging, or the like, to indefinitely maintain a pressurized state in the connected ring balloons 12-14 to keep the adjacent sleeve areas in fluidtight engagement with the stomach wall 31. Where desired, for example, to release fluids secreted by the stomach walls 31, the middle and lower ring balloons 13, 14 may be intermittently or permanently depressurized so that these fluids may pass through the remainder of the digestive tract. Alternatively, fluids secreted by the stomach area 31 shielded by the sleeve unit 10 may be aspirated through the oral cavity by way of the auxiliary lumens 23 and passages 26. Moreover, if desired, medicine may be carried into the annular zone defined between the sheath 11 and stomach walls 31 through the oral cavity by way of the auxiliary lumens 23 and passages 26.

The sleeve unit 10, by isolating the walls 31 of the stomach 32 from ingested food passing through it, reduces the digestive efficiency of the stomach. This results from interference with the normal contact of gastric juices, secreted by the stomach walls 31, on such food and the inability of the intestines of the lower digestive tract to absorb undigested food. Thus, the patient, while consuming food in even large quantities, is enabled to lose weight, since only a limited amount of the ingested food is ultimately absorbed.

Various other uses of the disclosed sleeve 10 or its equivalents are contemplated in the treatment of body disorders. For instance, the sleeve 10 may be disposed in the small intestine, rather than in the stomach, to directly reduce the effective area of the intestine available for absorption, again for the control of obesity. When disposed in the stomach, the sleeve may be utilized to medicate an ulcerous zone and isolate it from gastric juices to hasten normal recovery.

Figure 8:
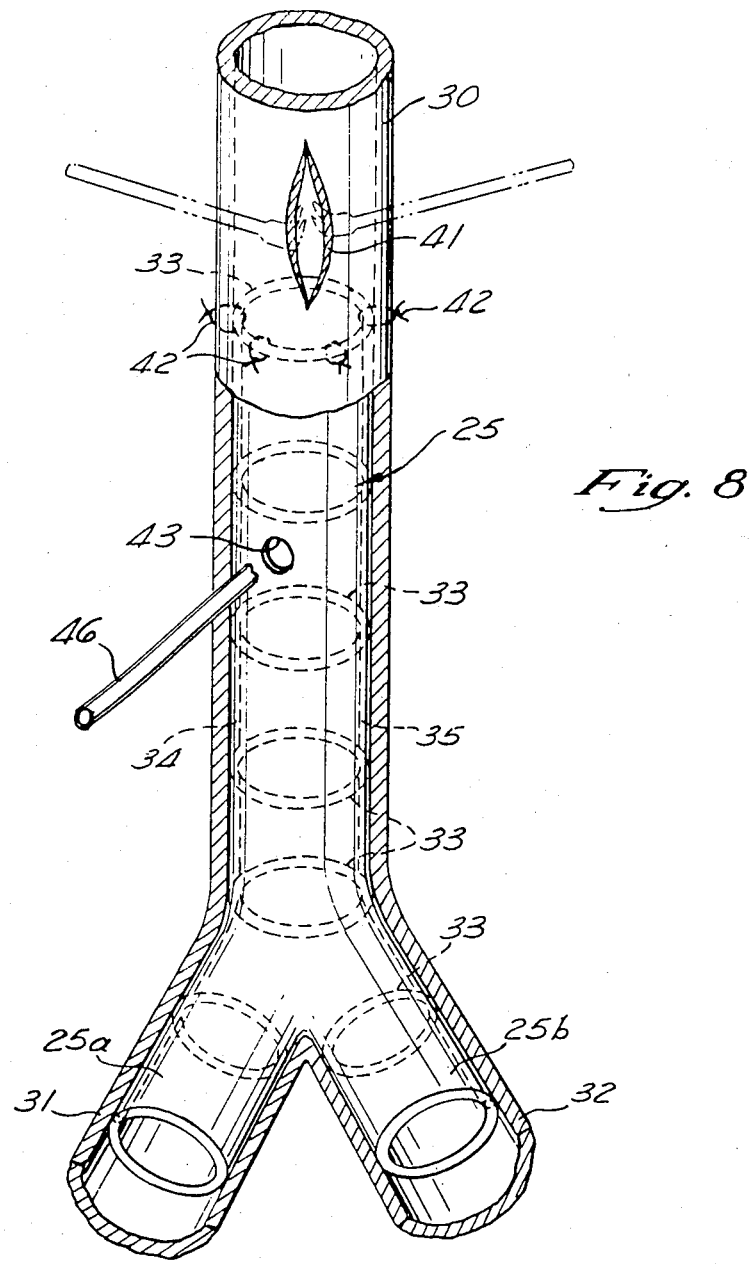
FIG. 8 is a schematic view of a second embodiment of the sleeve of the invention employed within an aorta.

Referring now to FIG. 8, there is shown a second embodiment of the invention wherein a sleeve 25 is disposed within a human aorta 30 and associated right and left common iliac arteries 31, 32. The sleeve 25 is bifurcated at one end to provide a pair of branches 25a and 25b corresponding to the right and left common iliac arteries 31, 32 respectively. The sleeve 25 has a construction essentially the same as the earlier-described sleeve 10. Ring balloons 33 are spaced axially along the sleeve including the branch portions 25a, 25b. Each of the ring balloons 33 is in fluid communication with at least one hollow filament 34,35 for purposes of inflation.

The sleeve 25 is advantageously employed in cases of advanced blood vessel disease where a patient's tissue is such that it is impossible to sew or anastomose it with grafts or artificial vessels. An incision 41 is made in the vessel 30 to allow the positioning of the sleeve 25 therein. The sleeve 25 is expanded into position by directing fluid pressure into the elongated filaments 34,35 in any suitable manner such as disclosed above with use of free extensions (not shown) of these filaments.

The sleeve 25 is anchored in the vessel 30, for example, by sutures 42 near the incision 41, while the distal portion of the sleeve remains free. One or more holes 43 may be cut into the wall of the sleeve prior to placement within the vessel to provide blood flow to various arterial branches 46. The sleeve 25 is preferably formed of relatively inelastic material or otherwise is circumferentially reinforced with inelastic material along its length so that the pressure of blood flowing through the sleeve is effectively isolated from the vessel 30.

Figure 9:
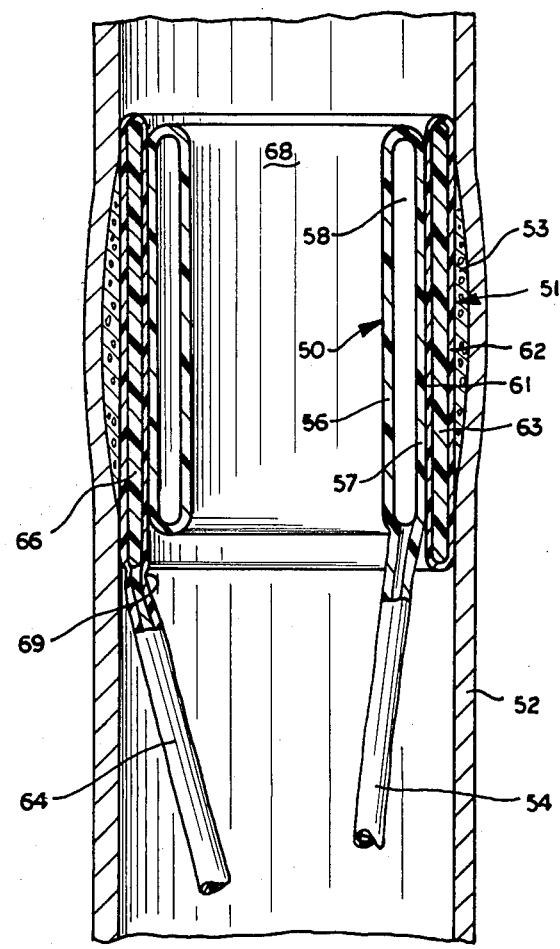
FIG. 9 is a sectional view in a longitudinal plane of a ring balloon and associated implantable sleeve disposed in a blood vessel of an animal body.

FIG. 9 illustrates another aspect of the invention wherein an inflatable ring balloon 50 is used to implant a prosthetic sleeve 51 at an area of a body vessel requiring expansion, reinforcement, isolation, or like treatment. The illustrated vessel 52 is a blood vessel previously blocked by plaque formation 53 and requiring expansion. A catheter 54 having a dilator annular balloon 50 at its free end and the sleeve 51 surrounding the balloon is threaded through the vessel 52 from an incision made in the vessel at a point remote from the area of plaque by known surgical procedures until the balloon and sleeve are within the area of blockage. When the balloon 50 and sleeve 51 are thus located within the plaque 53, the balloon is inflated to expand the plaque and the vessel 52. The balloon 50 has inner and outer imperforate walls 56, 57 which are circumferentially joined in a fluidtight manner at their ends. The annular space 58 between the sleeve walls 56 and 57 communicates with the lumen of the catheter tube 54. The balloon 50 is formed of any suitable plastic or rubber material which may be folded and/or expanded.

In a similar manner, the sleeve 51 has imperforate, flexible inner and outer walls 61,62 which are circumferentially joined in a fluidtight manner at their ends. An interior space 63 between the walls 61, 62 of the sleeve communicates with the interior of a tube 64 which extends along the catheter tube 54 to a point outside the vessel 52. The outer sleeve wall 62 may be formed of Dacron and can include a weave or mesh outer layer (not shown) which will lie against and adhere to the wall of the blood vessel. The inner wall 61 may be formed of Teflon so that cells will not readily adhere to this area.

The sleeve space 63 contains a fluid plastic material 66 which is caused to become solidified, preferably to a semirigid state after the balloon 50 has been expanded against the plaque 53. A suitable material for filling the sleeve space 63 Silastic 382, medical grade elastomer, marketed by Dow Corning Corporation, of Midland, Mich., U.S.A. This material originates as two separate liquids: an opaque viscous elastomer base and a catalyst. The elastomer base is composed of polydimethylsiloxane and silica. The stiffness of this silastic material is controllable by varying the percentage of silica used. The concentration of catalyst can be varied, as prescribed by the supplier, to control the working time from four to one hundred minutes, as desired. Preferably, the components of the material 66 are thoroughly mixed and subsequently introduced into the sleeve space 63 just prior to the catheterization operation in which the balloon 50, sleeve 51, and catheter 54 are inserted into the vessel.

When being manipulated along the vessel, the balloon 50 and sleeve 51 encircling it are in an uninflated, collapsed state. The collapsed state can be maintained by wrapping the sleeve 51 on itself and superficially heat-bonding it at appropriate folds. The balloon 50, once in position within the area of the vessel to be treated, is inflated with a gas or fluid supplied under pressure through the catheter 54. The pressure of this inflating fluid is sufficient to break the light heat bonds holding the folds of the sleeve 51 together and to expand the sleeve and plaque 53 in the vessel 52 to the required degree. The inflation pressure is maintained for a period sufficient for setting of the liquid 66 in the sleeve space 63 to become solidified into its semirigid state. A central passage 68 in the balloon 50 allows blood to continue to flow through the vessel 52 while the balloon is in place.

After the sleeve material 66 has solidifed into a semirigid structure, the balloon 50 is deflated through the catheter 54 and is withdrawn from the sleeve by pulling the catheter. The sleeve 51 remains in place, with the stiffness of the material 66 preventing collapse of the vessel 52, and reducing the risk of dislodgement of particles of plaque into the bloodstream.

The tube 64 allows any gas given off by the setting sleeve material 66 during its solidification to escape to the atmosphere. Once the solidification reaction is effectively completed, the tube 64 can be removed by pulling on it and causing it to sever from the sleeve 51 at a point 69, where it is connected to the sleeve where a frangible thin wall section may be provided in the wall of the tube for this purpose. It is contemplated that the catalyst for setting of the material 66 can be encapsulated and mixed with the base and caused to release from such encapsulation upon the pressure applied thereto by expansion of the balloon 50. Another alternative is to introduce the settable material 66, including mixed catalyst, into the space 63 through the tube 64 after the sleeve 51 has been manipulated into position.

The invention is not restricted to the slavish imitation of each and every detail set forth above. Obviously, devices may be provided which change, eliminate, or add certain specific details without departing from the scope of the invention.

What is claimed is:

1. A method of treating an area of a body vessel, comprising the steps of:

introducing a catheter with a collapsed inflatable annular balloon and a collapsed sleeve encircling the balloon on its end into the vessel at a point remote from the area to be treated;

manipulating the catheter axially along the vessel to cause the balloon and sleeve to enter the area to be treated;

inflating the balloon by introducing fluid under pressure into the balloon through a tube of the catheter in a manner wherein the sleeve surrounding the balloon is radially expanded towards the wall of the vessel;

providing in the sleeve a material which increases in rigidity after expansion of said balloon;

maintaining said balloon in an expanded condition in the vessel while said sleeve increases in rigidity and body fluid is allowed to pass through the central aperture of the balloon; and thereafter removing the balloon and catheter from the vessel and allowing the sleeve to remain in place in the area to be treated.

2. A method of treating an area of a body vessel, comprising the steps of:

introducing a catheter with a collapsed inflatable balloon and a collapsed sleeve encircling the balloon on its end into the vessel at a point remote from the area to be treated;

manipulating the catheter axially along the vessel to cause the balloon and sleeve to enter the area to be treated;

inflating the balloon by introducing fluid under pressure into the balloon through a tube of the catheter in a manner wherein the sleeve surrounding the balloon is radially expanded towards the wall of the vessel;

providing in the sleeve a material which increases in rigidity after expansion of said balloon;

maintaining said balloon in an expanded condition in the vessel while said sleeve increases in rigidity; and thereafter removing the balloon and catheter from the vessel and allowing the sleeve to remain in place in the area to be treated.

* * * * *